United States Patent [19]

Cook et al.

[11] Patent Number: 4,543,954

[45] Date of Patent: * Oct. 1, 1985

[54] EXERCISE RESPONSIVE CARDIAC PACEMAKER

[75] Inventors: William A. Cook, Bloomington; Neal E. Fearnot; Leslie A. Geddes, both of West Lafayette, all of Ind.

[73] Assignee: Purdue Research Foundation, West Lafayette, Ind.

[*] Notice: The portion of the term of this patent subsequent to Mar. 13, 2001 has been disclaimed.

[21] Appl. No.: 542,590

[22] Filed: Oct. 17, 1983

Related U.S. Application Data

[63] Continuation-in-part of Ser. No. 379,667, May 19, 1982, Pat. No. 4,436,092.

[51] Int. Cl.$^4$ .............................................. A61N 1/36
[52] U.S. Cl. .............................................. 128/419 PG
[58] Field of Search ....................... 128/419 P, 419 PG

[56] References Cited

U.S. PATENT DOCUMENTS

| | | | |
|---|---|---|---|
| 3,405,708 | 10/1968 | Webster | 128/692 |
| 3,545,428 | 12/1970 | Webster | 128/692 |
| 3,593,718 | 7/1971 | Krasner | 128/419 P |
| 3,726,269 | 4/1973 | Webster | 128/713 |
| 3,867,950 | 2/1975 | Fischell | 128/419 P |
| 3,877,438 | 4/1975 | Cannon | 128/419 PG |
| 3,921,642 | 11/1975 | Preston et al. | 128/419 PG |
| 4,153,048 | 5/1979 | Magrini | 128/692 |
| 4,201,219 | 5/1980 | Bozal Gonzalez | 128/419 PG |
| 4,202,339 | 5/1980 | Wirtzfeld et al. | 128/419 PG |
| 4,228,803 | 10/1980 | Rickards | 128/419 PG |
| 4,305,396 | 12/1981 | Wittkampf et al. | 128/419 PG |
| 4,313,422 | 2/1982 | Knudson et al. | 128/419 PG |
| 4,399,820 | 8/1983 | Wirtzfeld et al. | 128/419 PG |

FOREIGN PATENT DOCUMENTS 2609365  9/1977  Fed. Rep. of Germany.. 128/419 PG Primary Examiner—William E. Kamm
Assistant Examiner—Mitchell J. Shein
Attorney, Agent, or Firm—Woodard, Weikart, Emhardt & Naughton

[57] ABSTRACT

An exercise-responsive cardiac pacemaker is provided which physiologically controls the stimulation rate of a heart by sensing the venous blood temperature in the right ventricle of the heart. A temperature sensing means which includes a thermistor produces an output signal which is sent to an algorithm implementing means for implementing the output signal by an algorithm which represents the mathematical function between venous blood temperature in the right ventricle and heart rate in a normally functioning heart. The algorithm implementing means produces an output signal which is variable between a maximum and minimum level corresponding to the desired maximum and minimum levels of heart rate in a normally functioning heart. The algorithm implementing means is also programmable by telemetry after implantation. A cardiac pacemaker is connected to the algorithm implementing means and is responsive thereto in order to variably control the stimulation rate of the heart.

4 Claims, 10 Drawing Figures

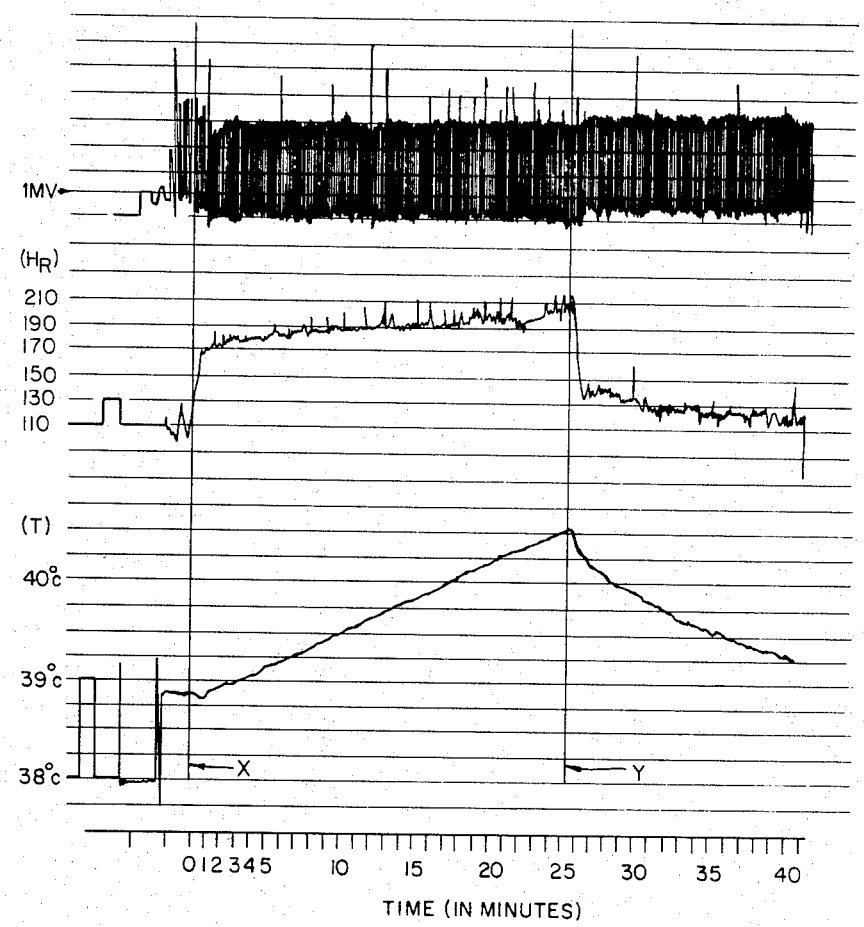

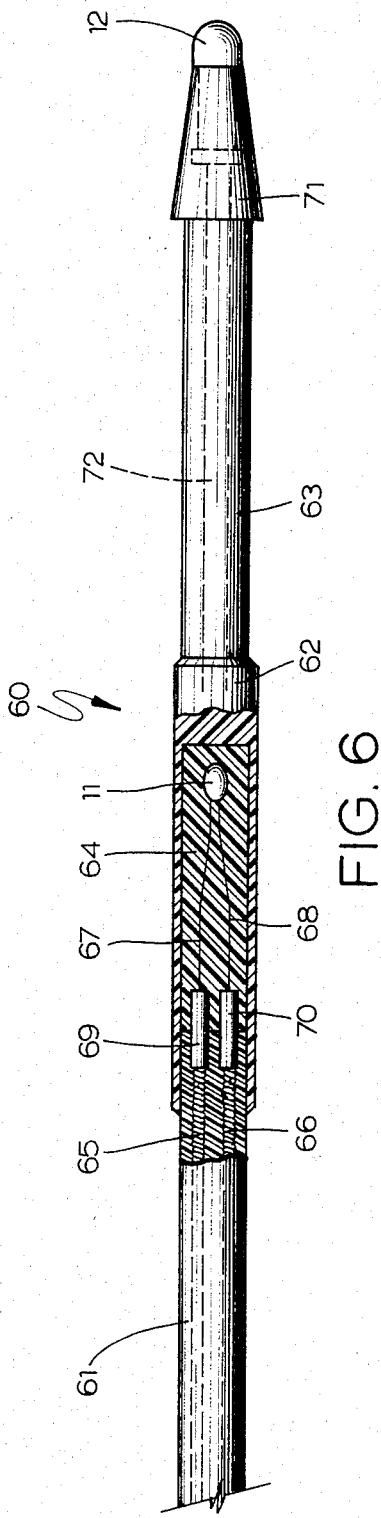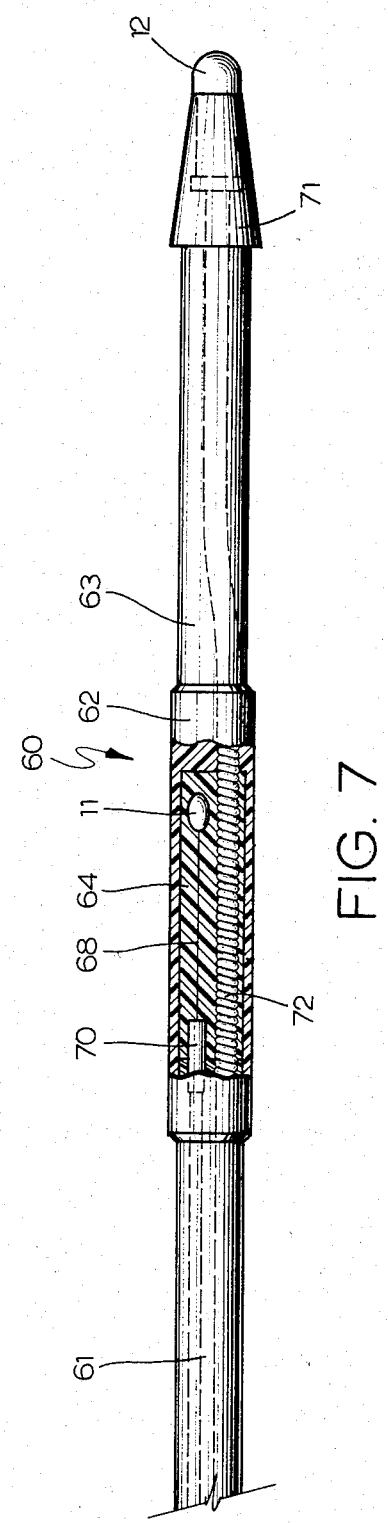

EXERCISE RESPONSIVE CARDIAC PACEMAKER

REFERENCE TO RELATED APPLICATIONS

This application is a continuation-in-part patent application of U.S. patent application Ser. No. 379,667 filed May 19, 1982 now U.S. Pat. No. 4,436,092.

BACKGROUND OF THE INVENTION

The present invention relates to a cardiac pacemaker device and method for physiologically controlling the stimulation rate of a heart within a body.

The human body is equipped to adapt to the increased need for cardiac output during exercise. If the heart is functioning properly, the nervous system increases the heart rate and reduces peripheral resistance in response to exercise. Typical cardiac pacemakers stimulate the heart at a fixed rate, and therefore cannot change in order to meet the increased need for cardiac output during exercise. Thus, a person using a typical cardiac pacemaker is somewhat constrained in his daily activities.

The typical fixed-rate cardiac pacemaker produces electrical stimuli at a rate of approximately 72 beats per minute. The stimuli are applied to the heart through an electrode system in contact with the heart wall. Each time the electrical stimulus is delivered by the pacemaker and applied to the heart wall, a contraction of the myocardium results. The contraction pumps blood to the body.

From the original fixed-rate cardiac pacemaker evolved the demand pacemaker. The demand pacemaker ceases to produce a stimulus when a spontaneous heart beat is detected. The presence of a spontaneous heart beat is indicated by a normal QRS complex in the electrocardiogram. Patients with intermittent conduction in the heart benefit from the demand pacemaker because this pacemaker does not compete with normal beats of the heart when and if they occur. Several modifications to the basic demand pacemaker have been made which attempt to better approximate a body's normal response. One such modified pacemaker allows the choice of two stimulation rates. Stimuli are produced at a nominal rate when the pacemaker is acting in the fixed-rate mode and at a lower rate when intermittent spontaneous heart beats are detected, thus allowing more time for the heart to beat spontaneously.

In addition to sensing the presence of electrical activity in the ventricle, sensing of atrial activity has also been used. A person may have normal atrial rhythm and some form of atrial-ventricular block. Such a person would benefit from an atrial-sensing pacemaker that delivers a stimulus to the ventricles after each atrial excitation. The atrial pacemaker has seen limited use because ventricular conduction problems often precipitate atrial tachycardia or fibrillation rendering the atrial-sensed pacemaker inactive.

In an effort to increase the efficiency of cardiac pacing, certain pacemakers use sensing of the electrogram in the atria and in the ventricles to allow atrial-ventricular synchrony to be restored. To produce each heart beat first the atria are stimulated. After a delay, nominally equal to the normal A-V node delay, the ventricles are stimulated. The addition of the atrial contraction produces the normal added filling of the ventricle that comes with synchronous atrial systole. Such a pacemaker, called the A-V sequential pacemaker, increases the end diastolic volume and therefore, the stroke volume, causing additional blood flow. In addition, A-V pacemakers incorporate dual sensing so that if the atria of ventricles beat, the spontaneously contracting chamber is not stimulated. More recently, a pacemaker with the combination of atrial and ventricular sensing, atrial and ventricular pacing, and atrial and ventricular inhibit has been developed. This pacemaker is commonly called a "DDD" pacemaker.

Pacemakers using each of the above modes may also be programmed after implantation. Each patient has slightly different requirements to optimally stimulate the heart. Therefore, if certain parameters of the pacemaker can be changed after implant, the pacemaker may be "individualized" to the patient's needs. Parameters that are programmable after implantation may include the rate, stimulus voltage, stimulus current, and electrogram sensitivity. In the case of the A-V sequential pacemaker, there is sensing and stimuli for both the atria and the ventricles that may be programmable in addition to the A-V delay time.

Since the first fixed-rate pacemaker, there have been many advances, but even with programmability the pacemaker does not adequately and reliably sense the body's need for more blood flow during exercise. Physiological pacemakers based on the electrical activity of the heart have not been applicable to a major portion of the pacemaker-using population. A patient with a partially denervated heart requires sensing of body cardiac output needs from a source other than electrical activity within the heart. There are many physiological indicators available from which the need for increased cardiac output may be sensed. In an attempt to provide sensing information, the nerves leading to the heart, in particular the sympathetic nerves, will provide information processed by the brain that naturally increases the heart rate. Unfortunately, current technology prohibits the use of a long term nerve impulse transducer.

The pH of the blood also has been measured and used to control the rate of a cardiac pacemaker. PH transducers that are implantable for long periods of time are however difficult to produce and therefore are not yet in common use.

The following list of references disclose devices which may have some general relevance to the present invention:

| Reference | Inventor |
| --- | --- |
| U.S. Pat. No. 3,867,950 | Fischell |
| U.S. Pat. No. 3,656,487 | Gobeli |
| U.S. Pat. No. 3,593,718 | Krasner |
| U.S. Pat. No. 3,828,371 | Purdy |
| U.S. Pat. No. 4,181,133 | Kolenik et al. |
| U.S. Pat. No. 4,023,121 | Alley, III |
| U.S. Pat. No. 4,228,803 | Rickards |
| U.S. Pat. No. 4,201,219 | Bozal Gonzalez |
| U.S. Pat. No. 4,202,339 | Wirtzfeld et al. |

*Journal of Association for Advancement of Medical Instrumentation*, "A Physiologically Controlled Cardiac Pacemaker", Krasner; Voukydis; and Nardella, Nov.–Dec. 1966, Pages 14–16, and 20.

U.S. Pat. No. 3,867,950 to Fischell discloses a fixed rate rechargeble cardiac pacemaker which utilizes as its power source a single rechargeable cell battery which is recharged through the patient's skin by magnetic induction. The electronic pulse generating circuitry is designed such that the output pulse rate varies as a function of the battery voltage and also as a function of the body temperature. This device is different from the present invention in that the heart stimulation rate is controlled by ambient body temperature, in other words, a body core temperature which represents the average body temperature. Thus, ambient body temperature is measured by a charging capacitor having a high temperature coefficient located within the pulse generator circuitry. Since ambient body temperature does not vary appropriately as a function of muscle exertion, this device will not respond to a body's need for increased cardiac output due to muscular exertion.

U.S. Pat. No. 3,656,487 to Gobeli discloses an electronic demand heart pacemaker with different pacing and standby rates. The device stimulates heart rate at a first frequency in the continued absence of natural heart beats but allows the heart to beat naturally at any rate above a second lower standby frequency. The device reverts to a third frequency in a non-demand type operation in the presence of an interfering electrical noise pattern.

U.S. Pat. No. 3,593,718 to Krasner discloses a physiologically controlled cardiac pacer which uses respiratory rate to vary the production of electronic pulses which are fed to a constant current source connected to the ventricle. In another variation, pulses are fed to two separate constant current sources, one connected to the atrium and the other, with delay, to the ventricle.

U.S. Pat. No. 3,828,371 to Purdy discloses a self-contained artificial heart which is adapted to vary the pulse rate and the stroke length in response to blood pressure. Variations in blood pressure are detected by means of a pressure sensitive transistor, thereby varying the rate of pumping of blood in response to blood pressure.

U.S. Pat. No. 4,181,133 to Kolenik et al. discloses a programmable tachycardia pacer which performs the dual functions of demand pacing as well as standby tachycardia break up. A command parameter control is used for programmably controlling the parameters of the pacer operation as well as of the tachycardia recognition and response.

U.S. Pat. No. 4,023,121 to Alley discloses an oscillator for a demand heart pacer which produces stimulation pulses in an inhibit mode at a first frequency and stimulation pulses at a second fixed rate mode at a second frequency. The device additionally employs an oscillator inhibitor which operates to define a variable second half of a refractory period to distinguish noise at a frequency approximately twice that of an acceptable heart frequency.

U.S. Pat. No. 4,228,803 to Rickards discloses a physiologically adaptive cardiac pacemaker having a demand generator which is sensitive to the electrical activity of the heart. The interval between a pacing stimulus delivered by a pacemaker generator and the evoked ventricular repolarization sets the escape interval of the generator for the subsequent stimulus, and thus physiologically controls the heart rate.

U.S. Pat. No. 4,201,219 to Bozal Gonzalez discloses a cardiac-pacemaker in which the generation of stimulation pulses is controlled by regulation signals detected in the nerves via receivers.

U.S. Pat. No. 4,202,339 to Wirtzfeld et al. discloses a cardiac pacemaker which measures the oxygen saturation of the blood as a control variable for influencing the frequency of stimulation. Determination of the blood oxygen saturation is made via light conductor probes implanted in the heart.

The publication entitled "A Physiologically Controlled Cardiac Pacemaker" by Krasner et al. discloses a cardiac pacemaker similar to that disclosed in U.S. Pat. No. 3,593,718 to Krasner, which uses respiratory rate to vary the production of electronic pulses to the heart.

One physiological indicator which responds directly to the need for higher cardiac output due to exercise, but which is not disclosed in any of the above references, is venous blood temperature. When a person exercises, the muscles do work. Since the muscles are not completely efficient, they also produce heat. It is the task of the blood stream to dispose of the additional heat produced by the exercising muscles.

The heat produced by a muscle raises the temperature of the blood leaving it. This blood returns directly to the right heart before passing through heat dissipating tissue. The blood returning to the right heart therefore contains information about the work output of the body musculature. Right ventricular blood is a combination of blood from the upper body via the superior vena cava and from the lower body via the inferior vena cava. The blood from these two areas of the body is mixed in the right atrium and again in the right ventricle where it is joined with blood drained from the heart. Thus, right ventricular blood temperature is the average temperature returning from all the body and so reflects the average work output of the body. Since the heat causing the temperature rise during exercise is generated by exercising muscles, the right ventricular blood temperature reflects the average level of exercise and, hence, the need for increased cardiac output or increased heart rate.

Accordingly, it is an object of the present invention to provide an improved cardiac pacemaker in which stimulation of the heart is varied in accordance with the level of muscular exertion.

This and other objects and advantages of the present invention will become more apparent in the following figures and detailed description.

SUMMARY OF THE INVENTION

One embodiment of the present invention includes a temperature sensing means for sensing a non-ambient body temperature which is related by an algorithm to heart rate in a normally functioning heart. The temperature sensing means is inserted into a desired location within a body wherein the temperature at said location is a non-ambient body temperature which is related to heart rate in a normally functioning heart by said algorithm. The temperature sensing means produces an output signal which is received by an algorithm implementing means connected to the temperature sensing means. The algorithm implementing means implements the output signal by an algorithm which represents the mathematical function between the non-ambient body temperature and heart rate in a normally functioning heart. A cardiac pacemaker is connected to the algorithm implementing means and is responsive thereto in order to variably control the stimulation rate of the heart.

BRIEF DESCRIPTION OF THE DRAWINGS

FIG. 1 is a graph of the electrogram of a body during periods of muscular exertion and rest.

FIG. 2 is a graph showing the relationship of right ventricular venous blood temperature with respect to time during periods of muscular exertion and rest.

FIG. 3 is a graph showing the relationship of heart rate with respect to time during periods of muscular exertion and rest.

FIG. 6 is a fragmentary elevation view, partially in section, showing the novel manner in which the temperature sensing means and pacing electrode are mounted to a catheter for placement within the heart.

FIG. 7 is a fragmentary elevation view, partially in section, of the FIG. 6 catheter assembly, rotated 90 degrees relative to FIG. 6.

DESCRIPTION OF THE PREFERRED EMBODIMENT

Figure 4:
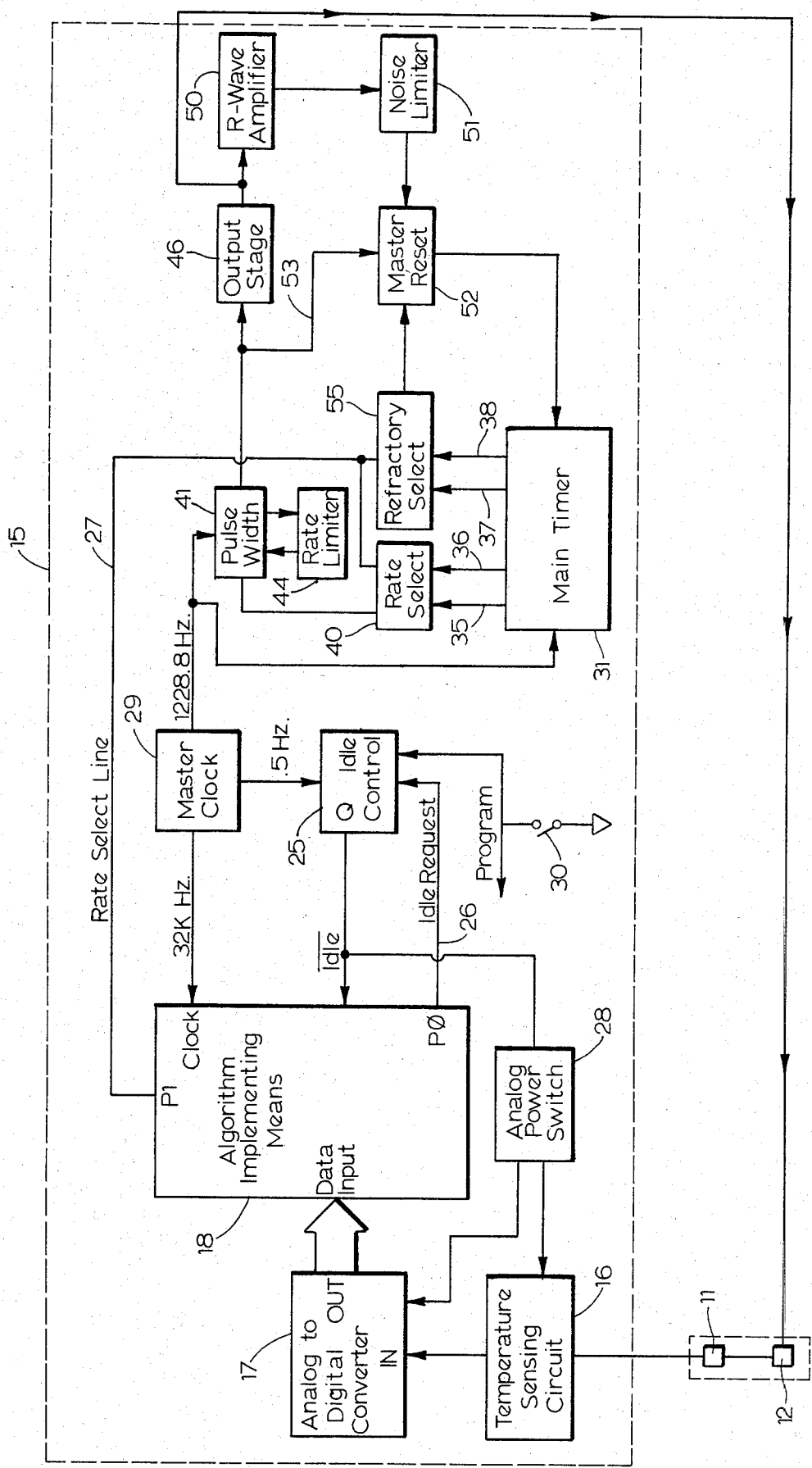
FIG. 4 is a schematic illustration of the pacing circuitry of the present invention in block diagram.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the act to which the invention relates.

It has been determined that there exists a relationship between a body's need for increased cardiac output due to exercise and venous blood temperature. Further, because blood entering the right ventricle of the heart is a combination of blood from the upper body via the superior vena cave and from the lower body via the inferior vena cava, the right ventricle is an appropriate location from which to determine the average temperature of blood returning from all of the body's musculature. It is important to note that this temperature will differ from body core temperature and therefore represents a non-ambient body temperature. FIGS. 1, 2, and 3 are typical graphs of the electrogram, right ventricular blood temperature, and heart rate, respectively, versus time in a normal test dog. Point X indicates the moment in time exercise was begun while Point Y indicates the moment in time exercise was ceased. It is readily observed from FIG. 3 that the heart rate increased with respect to time during the period of exercise and decreased with respect to time during the subsequent period of rest. FIG. 2 shows that the right ventricular blood temperature also increased with respect to time during the period of exercise and decreased with respect to time during the subsequent period of rest. As a result of a number of such tests on experimental test dogs, the following model equation has been derived which closely represents the relationship between right ventricular venous blood temperature and exercise rate:

$$T_i = a(T_{i-1} - T_0) + bE_i + T_0$$

In the above equation, $T_i$ is the temperature in degrees Centigrade at the sampled time interval i; $T_{i-1}$ represents the temperature in degrees Centigrade at the sampled time interval previous to interval i; $T_0$ represents the average right ventricular venous blood temperature in degrees Centigrade during rest; $E_i$ represents the exercise rate of the subject on a treadmill in miles per hour at interval i; a is a constant which represents the controlling termperature coefficient; and b is a constant which represents the controlling exercise coefficient.

Based upon the observed relationship between the heart rate and venous blood temperature in the right ventricle during different levels of exercise, a simple, practical, and implementable algorithm may be derived to produce a physiologically optimal heart rate. Thus, the relationship between venous blood temperature in the right ventricle and heart rate may be described by the following equation:

$$H_R = A + B(T - T_0) + C \text{ sign } (dT/dt)$$

In the above equation, $H_R$ represents the instantaneous heart rate in beats per minute; A represents the resting heart rate in beats per minute; B represents the slope of the heart rate verses temperature curve during exercise; T represents the smoothed or filtered instantaneous right ventricular temperature in degrees Centigrade; $T_0$ is the resting right ventricular temperature in degrees Centigrade; C represents the initial rise in the heart rate in beats per minute at the beginning of exercise divided by the slope of the temperature versus time curve during exercise; and dT/dt represents the derivative of temperature with respect to time.

At this point it should be noted that while the above equation was derived from experimental data on test dogs, this data generally agrees with data taken from human subjects and reported in the literature. The observed results are basically similar to the human data except that the slope of the temperature versus time curve in the human data suggests an exponential shaped increase in temperature versus time while the data on test dogs shows a near linear increase in temperature in many cases. This difference is probably because the human species perspires to dissipate excess heat while a dog dissipates heat by panting. Since perspiration is a much more efficient method for heat dissipation than panting, the heat dissipated by perspiration equals the excess heat produced by exercise at a lower temperature than by panting. Hence, the coefficients in the above equation and perhaps the form of the equation may by slightly different for human subjects.

Figure 5:
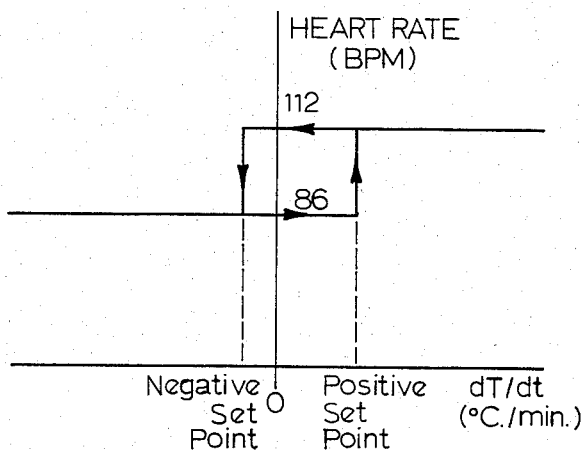
FIG. 5 is a graph of the control algorithm employed in the algorithm implementing means of the present invention with set points and hysteresis.

It should be also understood that other mathematical equations may be derived in order to approximate the observed relationship between venous blood temperature and heart rate, and thus may also be used as control algorithms. Further, the equation described above may be simplified while producing a slightly suboptimal response. FIG. 5 is a graph of the control algorithm used in the preferred embodiment of the present invention. It may be appreciated that this algorithm approximates the observed relationship between venous blood temperature and heart rate. In this control algorithm, however, the stimulus rate producing the instantaneous heart rate is allowed to assume only two discrete values representing the desired resting heart rate (86 BPM) and desired heart rate during exercise (112 BPM). The stimulus rate is a function of the time derivative of the instantaneous temperature dT/dt, and in order to give stability to the control algorithm, hysteresis is included in the set points for changing the stimulus rate. Since the temperature has been found to rise during exercise and fall immediately after exercise the time derivative of the temperature will be positive during exercise and negative after exercise. Thus, the stimulus rate changes to the exercise heart rate mode only if the time derivative of the temperature becomes more positive than the positive set point value. Further, once in the exercise heart rate mode, the stimulus rate reverts back to the resting heart rate mode only after the derivative of the time temperature becomes more negative than the negative set point value. In this manner, the effect of noise associated in calculating the time derivative of right ventricular temperature is minimized. It is to be understood that the set points in the control algorithm are constants which are determined by experimental data upon the particular subject for which the device of the present invention is to be used.

Referring now to FIG. 4, details of the operation and construction of the circuitry comprising the exercise responsive pacemaker of the present invention will now be described. The exercise-responsive pacemaker of the present invention is shown in a schematic block diagram generally designated at 10. Pacemaker 10 includes a thermistor 11 and pacing electrode 12 whose construction and operation will be described in more detail later herein. For the present, it is sufficient to note that thermistor 11 and pacing electrode 12 are adapted to be transvenously inserted within the right ventricle of a heart and are operatively connected to a pacer control circuit, generally designated at 15. Pacer control circuit 15 supplies stimulus pulses to the heart at a frequency which is controlled by right ventricular blood temperature, as sensed by thermistor 11, when natural pulses are not detected. It is to be understood that, although not shown, pacer control circuit 15 includes a suitable power source, which may be a battery, and that suitable connections between the power source and components of pacer control circuit 15 are also provided.

Referring now to the circuit components of pacer control circuit 15, it is seen that the output of thermistor 11 is connected to the input of temperature sensing circuit 16 which is a preamplifier circuit that linearizes the thermistor output verses temperature over the temperature range encountered by thermistor 11. Since the resistance across thermistor 11 varies in a known manner with temperature, the output voltage across temperature sensing circuit 16 is an analog representation of the instantaneous right ventricular blood temperature. The output of temperature sensing circuit 16 is connected to the input of analog to digital converter 17. Analog to digital converter 17 converts the analog input voltage from temperature sensing circuit 16 to a multiple bit data word. The digital output of analog to digital converter 17 is sent to algorithm implementing means 18 which implements the data received according to the control algorithm graphically depicted in FIG. 5. As previously mentioned, it is to be understood that the set points in the control algorithm are constants which are determined be experimental data upon the particular subject for which the device of the present invention is to be used. For this reason, algorithm implementing means 18 may be programmed by using conventionally known means such as programmable control chips. Programming algorithm implementing means 18 may be performed non-invasively by employing a parameter control circuit which is controlled externally by telemetric signals, such as is disclosed in U.S. Pat. No. 4,164,944 to Alley, et al. Other examples of programmable pacemakers are model numbers 325 and 325T programmable pacemakers produced by Cook Pacemaker Corporation of Leechburg, Pa.

The output of analog to digital converter 17 is sent to the input of algorithm implementing means 18 which samples the data once every two seconds based upon the receipt of a pulse from the Q output of idle control 25 which is located within algorithm implementing means 18. Idle control 25 thus serves as a wake-up circuit to switch on algorithm implementing means 18 and analog to digital converter 17 once every two seconds. In addition, idle control 25 controls analog power switch circuit 28 which controls the powering of temperature sensing circuit 16 and thermistor 11. The digital temperature values are stored in algorithm implementing means 18 for a period of two minutes, thus yielding a data base of 60 temperature values. The two minute period of temperature data is divided by algorithm implementing means 18 into two groups of 30 data representing sequential one minute periods. Algorithm implementing means 18 then calculates the average temperature for each of the two sequential one minute periods and subtracts the two average temperature values to yield an estimate of the slope or derivative of the temperature versus time. Of course, it is understood that when a new temperature datum is received by algorithm implementing means 18 the oldest datum stored in the data base is removed therefrom. Thus, the temperature derivative is recalculated by algorithm implementing means 18 every time a new temperature datum is received, which, as previously mentioned, occurs once every two seconds.

As soon as the new temperature datum has been stored in the memory of algorithm implementing means 18, idle request line 26 from algorithm implementing means 18 goes high, thereby resetting idle control 25 and changing the Q output of idle control 25 from high to low. As long as the Q output of idle control 25 stays low, algorithm implementing means 18 will not sample the output of analog to digital converter 17. This will not occur until another clock pulse is received at the set input of idle control 25 from the 0.5 Hz line of master clock 29. As was mentioned earlier herein, to give stability to the control algorithm, hysteresis is included in the decision or set points for changing the stimulus rate. The set points for the control algorithm are determined experimentally for each subject and programmed into algorithm implementing means 18. Algorithm implementing means 18 may be reprogrammed if necessary after implantation of pacemaker 10 by inputting the information through idle control 25 to algorithm implementing means 18 via read switch 30 which is externally activated between open and closed positions.

When algorithm implementing means 18 completes implementation of the control algorithm the desired instantaneous level of heart activity is determined and the output of rate select line 27 goes high or low corresponding to the exercise (high) heart rate mode or the resting (low) heart rate mode, respectively. The high or low signal is sent via select line 27 to rate select circuit 40. Main timer 31 continuously counts the clock pulses received from the 1228.8 Hz clock output line of master clock 29 and logically divides the clock pulses into four output pulses transmitted on lines 35–38, respectively, each line having a discrete predetermined pulse frequency. The frequencies of the two pulse streams traveling along lines 35 and 36 correspond to the desired frequency of heart stimulus at rest and during exercise, or 72 and 96 beats per minute, respectively, while the frequency of the pulses traveling along lines 37 and 38 correspond to the observed refractory periods associated with these two heart rates which are 312.5 milliseconds and 260.4 milliseconds, respectively. Lines 35 and 36 are connected at the input of rate select circuit 40 which logically determines in a well known manner which of the pulse frequencies on lines 35 and 36 will appear at its output based upon whether the logic signal present on select line 27 is high or low.

Once the signal corresponding to the stimulus rate is sent out from rate select circuit 40, the signal is received at the input of pulse width circuit 41 which changes the width of the incoming pulses to 0.81 milliseconds. Rate limiter circuit 44 is connected at its input and output to pulse width circuit 41 and limits the frequency of the pulses which are passed through pulse width circuit 41 to 500 milliseconds (120 bpm) in a well known manner. Thus, rate limiter circuit 44 serves to disable transmissions through pulse width circuit 41 which exceed a predetermined limit and which would be potentially injurious to the subject user. The output of pulse width circuit 41 is connected to output stage 46 which amplifies and shapes the incoming pulses from pulse width circuit 41 in a well known manner to provide the output to pacing electrode 12 for artificial stimulation of the heart.

The negative output terminal of output stage 46 is connected to the input of R-wave amplifier 50 which detects the R-wave or naturally occurring heart beat. R-wave amplifier 50 includes a high gain operational amplifier tuned to a bandpass of approximately 20 Hz to 100 Hz. The output of the operational amplifier is connected to a threshold comparator which checks and detects both positive and negative R-waves. If an R-wave is detected, R-wave amplifier 50 sends a signal to noise limiter 51 which prevents any frequencies greater than a fixed predetermined frequency from passing between R-wave amplifier 50 and master reset 52. In the embodiment shown, this predetermined threshold frequency is 39 milliseconds. Master reset 52 logically resets main timer 31 to zero in response to a signal from noise limiter 51 or from noise limiter bypass line 53, which serves to ensure that a signal will be sent to master reset 52 even if the R-wave is not passed through noise limiter 51 because the R-wave cannot be distinguished from noise. It may be noted that there exists some redundancy at the input of master reset 52 since in addition to detecting any natural heart beat R-wave amplifier 50 will also detect artificial pulses from output stage 46. Master reset 52 is normally disabled until it is enabled by a signal from the output of refractory select 55 which logically selects one of the two input signals on lines 37 and 38 based upon the high or low state of select line 27. Thus, once a natural or artificial stimulus is detected, master reset 52 is disabled for a period of time which corresponds to the refractory period of the heart at the selected stimulus rate. During this period, any signal received by master reset 52 will not cause a reset signal to be sent to main timer 29 since the heart muscles will not contract in response to an applied electrical stimulus during this period.

Reference will now be made to details of the construction of thermistor 11 and pacing electrode 12 of the present invention. FIG. 6 shows thermistor 11 and pacing electrode 12 attached to a catheter assembly 60 of suitable length which is principally comprised of a portion 61 of flexible plastic trilumen tubing and which, in the embodiment shown, has an outside diameter of approximately 0.110 inches. At this point it should be mentioned that the dimensions which are disclosed for the various elements comprising catheter assembly 60 refers to a construction which is sized for use in test dogs and will, of course, vary when adapted for use in the human species. The distal portion of catheter assembly 60 includes a plastic tubing portion 62 which houses thermistor 11, and a plastic tubing portion 63 connected to pacing electrode 12 by collar 71. Tubing portion 62 has an outer diameter of approximately 0.125 inches, while tubing portion 63 has an outside diameter of approximately 0.110 inches. Thermistor 11 is encased within a covering 64 of medical grade epoxy and received in the lumen of tubing portion 62 which is at least partially filled with an elastomer, such as type MDX4-4515 made by Dow Corning, as required to prevent relative movement of any elements within tubing portion 62. Thermistor 11 may be any conventionally known and suitable type, such as a type GA51J1 produced by Fenwall Electronics. Thermistor 11 is operatively connected to the pacing circuitry by a pair of bifilar wound coil wires 65 and 66 which are soldered to thermistor wires 67 and 68 within a pair of stainless steel tubing sections 69 and 70, respectively. It is also to be noted that, in the embodiment shown, thermistor 11 is located approximately 1.23 inches rearwardly of the exposed tip of pacing electrode 12. Pacing electrode 12 is operatively connected to the pacing circuitry by coil wire 72. Collar 71 is frustoconically shaped and flares outwardly away from pacing electrode 12 so as to facilitate transluminal insertion of catheter assembly 60 in a body. Further, collar 71 and pacing electrode 12 are shaped and sized such that the outer surface of their connection is smooth and contains no rough edge. Collar 71 may be made from any suitable material, such as for example, silicone and pacing electrode 12 may be made from a suitable electrode material, such as platinum.

It should be noted that, while not shown, suitable connector means is provided at the proximal end of catheter assembly 60 for coupling catheter assembly 60 to the control circuitry of pacemaker 10. The control circuitry of pacemaker 10 may be contained within a common housing or casing which is implanted subcutaneously. Alternatively, the control circuitry of pacemaker 10 may be a non-implantable unit which is located externally of the body to provide temporary artificial heart stimulation. In either case, stimulation of the heart is provided by pacing electrode 12 which stimulates the heart with an electrical stimulus having a frequency which is controlled by right ventricular blood temperature as sensed by thermistor 11.

Figure 8:
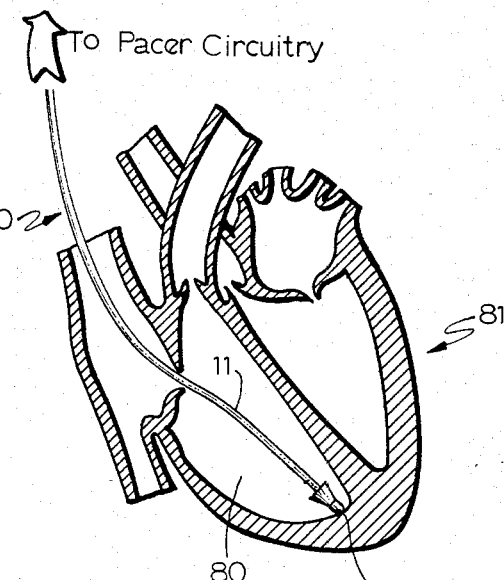
FIG. 8 is a fragmentary sectional view showing the placement of the temperature sensing means and pacing electrode within the right ventricle of a heart by catheterization of the right ventricle.

As depicted in FIG. 8, in order to use the device of the present invention in order to variably control the stimulation rate of the heart in accordance with the level of muscular exertion of the body, thermistor 11 and pacing electrode 12 are transvenously inserted, along with catheter 60 previously described, within the right ventricle 80 of a heart 81 employing suitable conventionally known catheterization techniques. Thermistor 11 is spaced sufficiently rearwardly of pacing electrode 12 such that when electrode 12 is properly positioned against the apex of the myocardium in order to provide artificial electrical stimulus to the heart, thermistor 11 is centrally positioned within right ventricle 80.

It may thus be appreciated that the arrangement of thermistor 11 and pacing electrode 12 together with catheter assembly 60 as herein disclosed permits the use of standard catheterization techniques in placement of thermistor 11 and pacing electrode 12 within the body. Further, the arrangement of thermistor 11 and pacing electrode 12 together with catheter assembly 60 as herein disclosed comprises a unitary construction which permits placement of thermistor 11 and pacing electrode 12 at the same time by performing one catheterization of the right ventricle. Thus, installation of the pacemaker of the present invention is no more complicated than that for other types of pacemakers now in use.

It should be obvious that the exercise responsive pacemaker of the present invention may be designed to provide any of the several types of heart stimulation techniques currently in use. For instance, pacemaker 10, may also be designed to perform as an A-V sequential pacemaker. In this application, sensing of the electrogram in the atrium and the ventricle is performed by an electrode in each respective chamber. Stimulation of the atria and ventricles can be provided as required in order to restore atrial-ventricular synchrony and to provide increased blood flow with increased levels of exertion. One type of A-V sequential pacemaker is disclosed in U.S. Pat. No. 4,192,316 to Walters, et al.

At this point it may be appreciated that the control algorithm of FIG. 5 may easily be adjusted to more closely correspond to the observed relationship between temperature and heart rate. For example, the control algorithm illustrated in FIG. 5 is a function only of the time derivative of the instantaneous temperature ($dT/dt$) and the artificial heart stimulus is capable of assuming only two distinct rates. The control algorithm may be made to more closely approximate the observed relationship between temperature and heart rate by allowing the set points to change based upon the instantaneous temperature. Thus, new set points may be chosen which make it more difficult for the stimulus rate to switch to the exercise heart rate mode when the instantaneous temperature is below a predetermined level. Also, in addition to changing the set points, the heart rate may also be incrementally increased or decreased at different temperature levels. Further, the derivative calculation may be made more optimal by decreasing the time span over which the derivative is calculated.

Figure 5A:
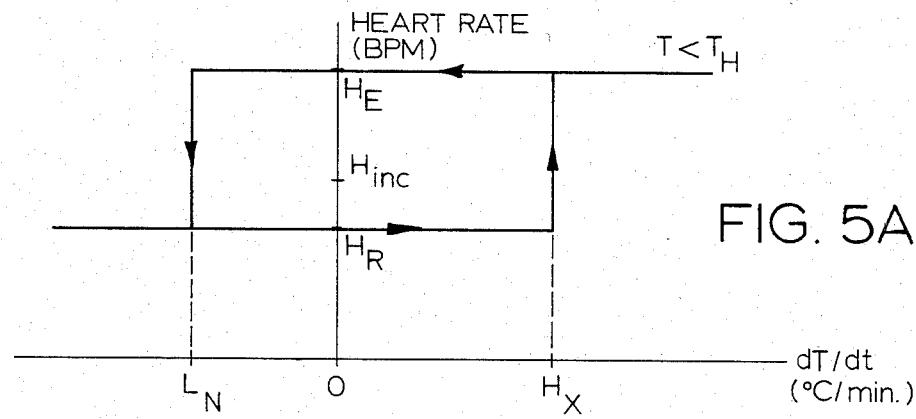
FIGS. 5A and 5B are graphs of an alternative embodiment of the control algorithm of FIG. 5 which more closely corresponds to the observed relationship between heart rate and right ventricular blood temperature.
Figure 5B:
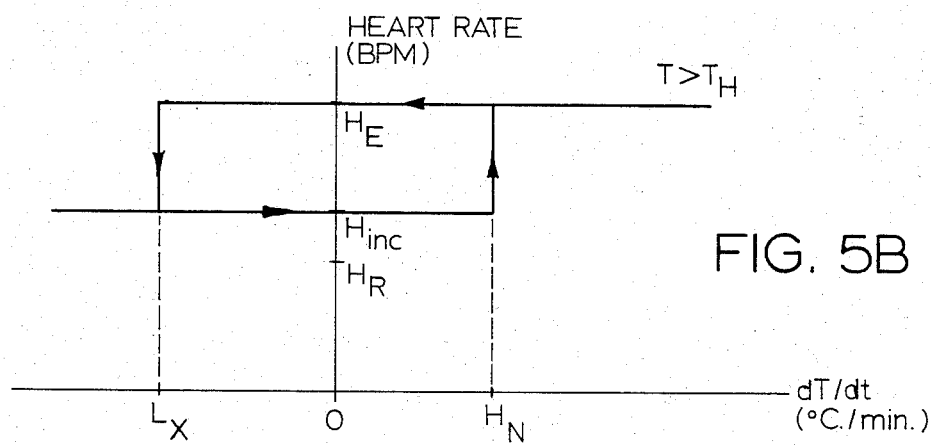

FIGS. 5A and 5B depict graphs of an alternative embodiment of the control algorithm used to approximate the observed relationship between heart rate and right ventricular blood temperature. Of course, it is understood that changes would have to be made to the control circuitry depicted in FIG. 4 in order to implement this control algorithm, but such changes are within the ordinary skill of those familiar in art and need not be described herein. In the control algorithm depicted in FIGS. 5A and 5B, the stimulus rate is capable of assuming three discrete rates, $H_R$ being the normal resting heart rate, $H_{inc}$ being the incrementally increased resting heart rate and $H_E$ being the exercise heart rate. Further, four set points or decision points are provided in this algorithm. $H_X$ and $H_L$ respectively correspond to the high heart rate maximum and minimum set points, while $L_X$ and $L_N$ are the low heart rate maximum and minimum set points, respectively. T is the instantaneous temperature of the subject and $T_H$ is a temperature value which exceeds the observed normal average resting temperature of the subject, but is intermediate within the temperature range of the subject encountered during exercise. A value for $T_H$ which is 1° centigrade greater than the normal average resting temperature has been found suitable for test dogs. The set point values are chosen so that it is more difficult for the stimulus rate to go to the exercise heart rate $H_E$ when the temperature is below $T_H$, and more difficult to go to the incrementally increased resting heart rate $H_{inc}$ when the temperature is above $T_H$ than it is to go to the normal resting heart rate when the temperature is below $T_H$.

Thus, for instantaneous temperatures below $T_H$ (FIG. 5A), the artificial stimulus rate is capable of assuming two discrete frequency levels corresponding to the desired resting heart rate $H_R$ and the desired exercise heart rate $H_E$. At temperatures above $T_H$ the resting heart rate is increased by a desired amount, such as 10 beats per minute, to correspond to $H_{inc}$. This incrementally increased resting heart rate may also be termed the "fever" rate. Using this control algorithm, it is not possible for the artificial stimulus rate to switch down to the lowest resting heart rate $H_R$ until the instantaneous temperature decreases to below $T_H$.

It is easily appreciated that the control algorithm shown in FIGS. 5A and 5B offers increased flexibility of response to the body's need for increased heart output since there distinct stimulus rates are capable of being produced. Further, it should be obvious that by using the method just described, an even more optimal control algorithm implementing more than three artificial stimulus rates can also be derived.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A cardiac pacemaker including means for variably controlling the stimulation rate of the heart according to the level of muscular exertion in the body, comprising:

a sensor means for sensing a body temperature;

a stimulus means for applying an electrical stimulus to a heart;

a control circuit means for calculating $dT/dt$ of said sensed body temperature, said control circuit means including means for generating a rate control signal according to a predetermined algorithm relating heart rate to $dT/dt$; and a cardiac pacemaker connected to said control circuit means and said stimulus means and responsive to said rate control signal to variably control the stimulation rate of the heart.

2. The cardiac pacemaker of claim 1 wherein said rate control signal generating means is operative to generate a rate control signal according to a predetermined algorithm relating heart rate to $dT/dt$ and a previous heart rate.

3. The cardiac pacemaker of claim 2 wherein said control circuit means is operative to calculate $dT/dt$ on the basis of first and second average temperature values associated respectively with first and second consecutive time periods of approximately one-minute duration.

4. The cardiac pacemaker of claim 3 wherein said control circuit means further includes means for sampling the output of said sensor means periodically at a rate of approximately one sample every two seconds, and means for averaging temperature samples from said sensor means over a period of approximately one minute.

* * * * *

UNITED STATES PATENT AND TRADEMARK OFFICE

CERTIFICATE EXTENDING PATENT TERM
UNDER 35 U.S.C. 156

Patent No.     : 4,543,954

Dated          : October 1, 1985

Inventor(s)    : William A. Cook et al

Patent Owner   : Purdue Research Foundation

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

410 DAYS with all rights pertaining thereto as provided by 35 USC 156 (b).

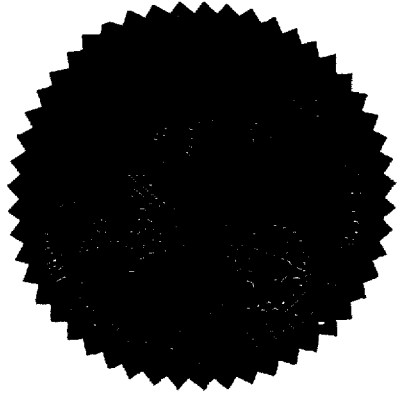

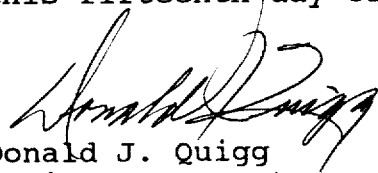

I have caused the seal of the Patent and Trademark Office to be affixed this fifteenth day of June 1989.

Donald J. Quigg
Assistant Secretary and Commissioner
of Patents and Trademarks